United States Patent
Vijil et al.

(10) Patent No.: US 12,079,730 B2
(45) Date of Patent: Sep. 3, 2024

(54) TRANSFER LEARNING FOR MOLECULAR STRUCTURE GENERATION

(71) Applicant: International Business Machines Corporation, Armonk, NY (US)

(72) Inventors: Enara C Vijil, Millwood, NY (US); Payel Das, Yorktown Heights, NY (US); Inkit Padhi, White Plains, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 1098 days.

(21) Appl. No.: 16/886,160

(22) Filed: May 28, 2020

(65) Prior Publication Data
US 2021/0374551 A1    Dec. 2, 2021

(51) Int. Cl.
G06N 3/088    (2023.01)
G06N 3/045    (2023.01)
G06N 3/047    (2023.01)
G16C 20/70    (2019.01)

(52) U.S. Cl.
CPC ............ *G06N 3/088* (2013.01); *G06N 3/045* (2023.01); *G06N 3/047* (2023.01); *G16C 20/70* (2019.02)

(58) Field of Classification Search
CPC .. G06F 18/24143; G06N 3/045; G06N 3/047; G06N 3/088; G16C 20/50; G16C 20/70
See application file for complete search history.

(56) References Cited

U.S. PATENT DOCUMENTS

| 2011/0161265 A1 | 6/2011 | Gustasson et al. |
| 2011/0236429 A1 | 9/2011 | Hancock et al. |
| 2013/0252280 A1 | 9/2013 | Weaver et al. |
| 2015/0142408 A1 | 5/2015 | Futamura |

(Continued)

FOREIGN PATENT DOCUMENTS

| CN | 108694991 A | 10/2018 |
| CN | 110317248 A | 10/2019 |

(Continued)

OTHER PUBLICATIONS

Das et al., "Accelerating Antimicrobial Discovery with Controllable Deep Generative Models and Molecular Dynamics", May 22, 2020, arXiv:2005.11248v1 [cs.LG], pp. 1-57 (Year: 2020).*

(Continued)

*Primary Examiner* — Brent Johnston Hoover
(74) *Attorney, Agent, or Firm* — Amin, Turocy & Watson, LLP

(57) ABSTRACT

Techniques regarding generating molecular structures with attributes of interest are provided. For example, one or more embodiments described herein can comprise a system, which can comprise a memory that can store computer executable components. The system can also comprise a processor, operably coupled to the memory, and that can execute the computer executable components stored in the memory. The computer executable components can comprise a transfer learning component that determines a molecular structure of a compound by employing a transfer learning process that utilizes lessons learned from an unconditional generative machine learning model to train a conditional machine learning model that regards a target attribute profile.

20 Claims, 12 Drawing Sheets

(56) References Cited

U.S. PATENT DOCUMENTS

| | | | |
|---|---|---|---|
| 2017/0161635 | A1 | 8/2017 | Oono et al. |
| 2019/0010533 | A1 | 1/2019 | Wong |
| 2019/0018933 | A1 | 1/2019 | Oono et al. |
| 2019/0252036 | A1 | 8/2019 | Elemento et al. |
| 2019/0304568 | A1 | 10/2019 | Wei et al. |
| 2019/0362816 | A1 | 11/2019 | Statsyuk |
| 2019/0392304 | A1 | 12/2019 | Aliper et al. |
| 2020/0020415 | A1 | 1/2020 | Sarmiento et al. |

FOREIGN PATENT DOCUMENTS

| | | |
|---|---|---|
| CN | 111081316 A | 4/2020 |
| WO | 2018220368 A1 | 12/2018 |
| WO | 2019081781 A1 | 5/2019 |

OTHER PUBLICATIONS

Ionavac et al., "Simpler is Better: How Linear Prediction Tasks Improve Transfer Learning in Chemical Autoencoders", Apr. 8, 2020, The Journal of Physical Chemistry A 2020 124 (18), pp. 3679-3685 (Year: 2020).*
Li, et al. "Multi-objective de novo drug design with conditional graph generative model" J Cheminform (2018) 10:33, https://jcheminf.biomedcentral.com/track/pdf/10.1186/s13321-018-0287-6. 24 pages.
amr-review.org,, "Review on Antimicrobial Resistance," Retrieved from the Internet: Mar. 17, 2020, https://amr-review.org/, 2 pages.
Mourtada, et al., "Design of stapled antimicrobial peptides that are stable, nontoxic and kill antibiotic-resistant bacteria in mice," Nat Biotechnol 37, pp. 1186-1197, 2019.
Das et al., "PepCVAE: Semi-Supervised Targeted Design of Antimicrobial Peptide Sequences," (Submitted on Oct. 17, 2018 (v1), last revised Nov. 13, 2018 (this version, v3), https:/arxiv.org/abs/1810.07743.
Mondal, "A brief appraisal of computational modeling of antimicrobial peptides' activity." Drug Dev Res., vol. 80, No. 1., pp. 28-32, Feb. 2019.
Müller et al., "Recurrent Neural Network Model for Constructive Peptide Design." J. Chem. Inf. Model., 58, 2, pp. 472-479, 2018.
Witten, "Deep learning regression model for antimicrobial peptide design." bioRxiv 692681, Posted Jul. 12, 2019. https://www.biorxiv.org/content/10.1101/692681v1.abstract.
Nagarajan, et al., "Computational antimicrobial peptide design and evaluation against multidrug-resistant clinical isolates of bacteria," JBC Papers in Press. Published on Dec. 19, 2017 as Manuscript M117.805499, http://www.jbc.org/cgi/doi/10.1074/jbc.M117.805499.
Mell, Peter, et al. "The NIST Definition of Cloud Computing." National Institute of Standards and Technology. Sep. 2011. 7 pages.
Non-Final Office Action received for U.S. Appl. No. 16/880,021 dated Feb. 10, 2023, 93 pages.
Lee et al., "What can machine learning do for antimicrobial peptides, and what can antimicrobial peptides do for machine learning?", Interface Focus, vol. 7, 2017, 14 pages.
Fjell et al., "Identification of Novel Antibacterial Peptides by Chemoinformatics and Machine Learning", J. Med. Chem., vol. 52, 2009, pp. 2006-2015, 10 pages.
Mátyus et al., "Computer Simulation of Antimicrobial Peptides", Current Medicinal Chemistry, 2007, vol. 14, pp. 2789-2798, 11 pages.
Non-Final Office Action received for U.S. Appl. No. 17/487,225 dated Feb. 17, 2023, 62 pages.
Kumar et al., "Antimicrobial Peptides: Diversity, Mechanism of Action and Strategies to Improve the Activity and Biocompatibility in Vivo", Biomolecules, 2018, vol. 8, No. 4, 24 pages.
Lowe, Derek, "Not alphafold's fault" Blog "In the pipeline", entry of, Sep. 7, 2022, 6 pages.
Non Final office action received for U.S. Appl. No. 16/880,280 dated Mar. 19, 2021, 113 pages.
French et al., "What is a conservative substitution?",J. Mol. Evol. (1983) vol. 19, pp. 171-175.
CAS Registry: Exact and pattern searching of protein sequences Nov. 2008, 30 pages.
Maraj et al., "Evaluation of hemolysis in patients with prosthetic heart valves.", Echocardiography Laboratory, Division of Cardiology, Albert Einstein Medical Center, Temple University School of Medicine, Philadelphia, Pennsylvania, USA Clin. Cardiol. (1998), vol. 21, pp. 387-392.
Phoenix et al., "The hydrophobic moment and its use in the classification of amphiphilic structures.", Mol Membr Biol Downloaded from informahealthcare.com by UB Kiel on Oct. 23, 2014 For personal use only, Molecular Membrane Biology. (2002) vol. 19, pp. 1-10.
Yampolsky et al., "The Exchangeability of Amino Acids in Proteins.", DOI: 10.1534/genetics.104.039107, Genetics (2005), pp. 1459-1472.
Kingma et al., "Auto-Encoding Variational Bayes" arXiv:1312.6114v10m, May 1, 2014, 14 pages.
Bowman et al., "A large annotated corpus for learning natural language inference", arXiv:1508.05326, Aug. 21, 2015, 11 pages.
Hochreiter et al., "Long Short—Term Memory", Neural computation vol. 9, No. 1, 1997, pp. 32.
Bowman et al., "Generating Sentences from a Continuous Space", arXiv preprint arXiv:1511.06349, May 12, 2015, 12 pages.
Tolstikhin et al.,"Wasserstein Auto-Encoders", arXiv preprint arXiv:1711.01558, Dec. 5, 2017, 20 pages.
Bahuleyan et al., "Stochastic Wasserstein Autoencoder for Probabilistic Sentence Generation" arXiv:1806.08462, Apr. 12, 2018, 9 pages.
Makhzani et al., "Adversarial Autoencoders" arXiv:1511.05644, May 25, 2015, 16 pages.
Gretton et al., "A Kernel Method for the Two-Sample-Problem", Advances in neural information processing systems, 2007, 8 pages.
Rahimi et al., "Unsupervised Regression with Applications to Nonlinear System Identification", Advances in neural Information processing systems, 2007, 8 pages.
Rubenstein et al., "On the Latent Space of Wasserstein Auto-Encoders", arXiv:1802.03761 , Feb. 11, 2018, 9 pages.
Theis et al., "A Note On The Evaluation of Generative Models", ICLR, Apr. 24, 2016, 10 pages.
Alemi, et al.,"Fixing a Broken ELBO" arXiv:1711.00464, Feb. 13, 2017, 21 pages.
Ranzato et al., "Sequence Level Training with Recurrent Neural Networks", arXiv preprint arXiv:1511.06732, May 6, 2015, 16 pages.
Bengio et al., "Scheduled Sampling for Sequence Prediction with Recurrent Neural Networks", Advances in Neural Information Processing Systems, 2015, 9 pages.
Zhao et al., "Adversarially Regularized Autoencoders", arXiv:1706.04223, Jun. 29, 2017, 16 pages.
Merity et al., "Regularizing and Optimizing LSTM Language Models", arXiv preprint arXiv:1708.02182, Aug. 7, 2017, 10 pages.
Yu et al., "SeqGAN: Sequence Generative Adversarial Nets with Policy Gradient", Thirty-First AAAI Conference on Artificial Intelligence, 2017, pp. 2852-2858.
Guimaraes et al., ,"Objective-Reinforced Generative Adversarial Networks (ORGAN) for Sequence Generation Models" arXiv preprint arXiv:1705.10843, Feb. 7, 2017, 7 pages.
Jang et al., "Categorical Reparameterization with Gumbel-Softmax", arXiv:1611.01144, Aug. 5, 2017, 13 pages.
Kusner et al., "GANS for Sequences of Discrete Elements with the Gumbel-softmax Distribution", arXiv:1611.04051, Nov. 12, 2016, 6 pages.
Maddison et al., "The Concrete Distribution: A Continuous Relaxation of Discrete Random Variable", arXiv:1611.00712, Mar. 5, 2017, 20 pages.
Zhang et al., "Generating Text via Adversarial Training", Workshop on Adversarial Training, NIPS 2016, Barcelona, Spain, 2016, 6 pages.
Kingma et al., "Semi-supervised Learning with Deep Generative Models", Advances in Neural Information Processing Systems, 2014, 9 pages.

(56) References Cited

OTHER PUBLICATIONS

Hu et al., "Toward Controlled Generation of Text", International Conference on Machine Learning, 2017, 10 pages.

Engel et al., "Latent Constraints: Learning To Generate Conditionally From Unconditional Generative Models", Dec. 21, 2017, arXiv:1711.05772, 22 pages.

Dathathri et al., "Plug And Play Language Models: A Simple Approach To Controlled Text Generation", arXiv preprint arXiv:1912.02164, Mar. 3, 2020, 34 pages.

Bombarelli et al., "Automatic Chemical Design Using a Data-Driven Continuous Representation of Molecules", ACS central science, vol. 4, Jun. 14, 2018, pp. 268-276.

Zhou et al., "Optimization of Molecules via Deep Reinforcement Learning", Scientific reports, vol. 9, Jul. 24, 2019, 10 pages.

You et al., "Graph Convolutional Policy Network for Goal-Directed Molecular Graph Generation" Advances in Neural Information Processing Systems, 2018, 12 pages.

Popova et al., "Deep reinforcement learning for de novo drug design", Science advances, Jul. 26, 2018, vol. 4, 15 pages.

Zhavoronkov et al., "Deep learning enables rapid identification of potent DDR1 kinase inhibitors", Nature Biotechnology, vol. 37, Sep. 2019, pp. 1038-1046.

Korovina et al., "ChemBO: Bayesian Optimization of Small Organic Molecules with Synthesizable Recommendations" arXiv:1908.01425v2, Oct. 22, 2019, 19 pages.

Lim et al., "Molecular generative model based on conditional variational autoencoder for denovo molecular design", vol. 10. No. 31, 2018, 9 pages.

Kang et al., "Conditional molecular design with deep generative models", Journal of chemical information and modeling, vol. 59, No. 43, Jul. 18, 2018, 27 pages.

Li et al., "Multi-objective de novo drug design with conditional graph generative model", vol. 10, No. 33, 2018, 24 pages.

Sib S, Universal Protein Resource (UniProt), https://www.uniprot.org, (2018) 2 pages.

Singh et al., "SATPdb: a database of structurally annotated therapeutic peptides", Nucleic acids research, Nov. 2, 2015, pp. 1119-1126.

Pirtskhalava et al., "DBAASP v.2: an enhanced database of structure and antimicrobial/cytotoxic activity of natural and synthetic peptides" Nucleic acids research, vol. 44, 2015, pp. 1104-1112.

Khurana et al., "DeepSol: a deep learning framework for sequence-based protein solubility prediction" Bioinformatics, vol. 34, No. 15, Mar. 15, 2018, pp. 2605-2613.

Bhadra et al., "AmPEP: Sequence-based prediction of antimicrobial peptides using distribution patterns of amino acid properties and random forest", Scientific reports, Jan. 26, 2018, 10 pages.

Gupta et al., "In Silico Approach for Predicting Toxicity of Peptides and Proteins", PloS one, vol. 8, No. 9, Sep. 2013, 10 pages.

Frishman et al., "Knowledge-Based Protein Secondary Structure Assignment", Proteins: Structure, Function, and Genetics vol. 23, 1995, pp. 566-579.

Tien et al., "PeptideBuilder: A simple Python library to generate model peptides", Peerj, May 21, 2013, 10 pages.

Jong et al., "Improved Parameters for the Martini Coarse-Grained Protein Force Field", Journal of Chemical Theory and Computation, Jul. 25, 2012, 11 pages.

Wassenaar et al., "Computational Lipidomics with insane: A Versatile Tool for Generating Custom Membranes for Molecular Simulations", Journal of Chemical Theory and Computation, Apr. 10, 2015, pp. 2144-2155.

Marrink et al., "The MARTINI Force Field: Coarse Grained Model for Biomolecular Simulations", The Journal of Physical Chemistry, vol. 111, Apr. 25, 2007, pp. 7812-7824.

Berendsen et al., "GROMACS: A message-passing parallel molecular dynamics implementation", Computer Physics Communications vol. 91, Dec. 2, 1994, pp. 43-56.

Abraham et al., "GROMACS: High performance molecular simulations through multi-level parallelism from laptops to supercomputers", SoftwareX 1-2, Jun. 25, 2015, 7 pages.

Bussi et al., "Canonical sampling through velocity rescaling", The Journal of Chemical Physics, vol. 126, Jan. 3, 2007, 8 pages.

Parrinello et al., "Polymorphic transitions in single crystals: A new molecular dynamics method", Journal of Applied Physics vol. 52, Aug. 14, 1981, pp. 7182-7190.

Nose et al., "Constant pressure molecular dynamics for molecular systems", Molecular Physics vol. 50, 1983, pp. 1055-1076.

Huang et al., "CHARMM 36m: an improved force field for folder and intrinsically disordered proteins", Nov. 7, 2016, Nature Methods, vol. 14, 6 pages.

Qin et al., "Artificial intelligence method to design and fold alphahelical structural proteins from the primary amino acid sequence", Extreme Mechanics Letters, 2020, 26 pages.

Jo et al., "CHARMM-GUI Membrane Builder for Mixed Bilayers and Its Application to Yeast Membranes", Biophysical Journal vol. 97, Jul. 2009, pp. 50-58.

Humphrey et al., "VMD: Visual Molecular Dynamics", Journal of Molecular Graphics, vol. 14, Feb. 1996, pp. 33-38.

Phillips et al., "Scalable Molecular Dynamics with NAMD", May 26, 2005, pp. 1781-1802.

Muller et al., "modIAMP: Python for antimicrobial peptides", Bioinformatics, vol. 33, No. 17, 2017, pp. 2753-2755.

Yu et al., The compositional adjustment of amino acid substitution matrices, Proceedings of the National Academy of Sciences, vol. 100, No. 26, Dec. 23, 2003, 15688-15693.

Cock et al., "Biopython: freely available Python tools for computational molecular biology and bioinformatics", Bioinformatics vol. 25, No. Mar. 11, 20, 2009, pp. 1422-1423.

Madden, Thomas., "The BLAST Sequence Analysis Tool", The NCBI Handbook [Internet]. 2nd edition (National Center for Biotechnology Information (US), Mar. 15, 2013, 10 pages.

Chin et al., "A macromolecular approach to eradicate multidrug resistant bacterial infections while mitigating drug resistance onset", Nature communications, vol. 9, No. 1, 2018, 14 pages.

Ng et al., "Synergistic Co-Delivery of Membrane-Disrupting Polymers with Commercial Antibiotics against Highly Opportunistic Bacteria", Advanced Materials, vol. 25, 2013, pp. 6730-3736.

Liu et al., "Highly potent antimicrobial polyionenes with rapid killing kinetics, skin biocompatibility and in vivo bactericidal activity", Biomaterials, vol. 127, Feb. 28, 2017, pp. 36-48.

International Search Report and Written Opinion received for PCT Application Serial No. PCT/IB2021/054139 dated Aug. 24, 2021, 12 pages.

Final Office Action received for U.S. Appl. No. 17/487,225 dated Jun. 26, 2023, 96 pages.

Narayan et al., "Thermally Versus Chemically Denatured Protein States", Biochemistry, vol. 58, 2019, 2519-2523.

Gonzalez et al., "Force Fields and Molecular Dynamics Simulations", Collection SFN, vol. 12, 2011, 32 pages.

Makai et al., "Sturcure and Drug Release of Lamellar Liquid Crystals Containing Glycerol", International Journal of Pharmaceutics, vol. 256, 2003, 95-107.

Myers et al., "Trifluoroethanol Effects on Helix Propensity and Electrostatic Interactions in the Helical Peptide from Ribonuclease T1", Protein Science, vol. 7, 1988, 383-388.

Rowlett et al., "Impact of Membrane Phospholipid Alterations in *Escherichia coli* on Celluylar Function and Bacterial Stress Adaptation", Journal of Bacteriology, vol. 199, Issue 13, Jul. 2017, 22 pages.

Final Office Action received for U.S. Appl. No. 16/880,021 dated Jul. 27, 2023, 43 pages.

Starr et al., "Synthetic Molecular Evolution of Host Cell-compatible, Antimicrobial Peptides Effective Against Drug-resistant, Biofilm-forming Bacteria", PNAS, vol. 117, No. 15, Apr. 14, 2020, 8437-8448.

STN, "CAS Registry: Exact and Pattern Searching of Protein Sequences", American Chemical Society, Nov. 2008, 33 pages.

Advisory Action received for U.S. Appl. No. 16/880,021 dated Sep. 19, 2023, 37 pages.

Veltri et al., "Improving Recognition of Antimicrobial Peptides and Target Selectivity Through Machine Learning and Genetic Programming", IEEE/ACM transactions on computational biology and bioinformatics, vol. 14, No. 2, 2015, pp. 300-313.

(56) References Cited

OTHER PUBLICATIONS

Kakumani et al., "A Two-Stage Neural Network based Technique for Protein Secondary Structure Prediction", 2008 30th Annual International Conference of the IEEE Engineering in Medicine and Biology Society. IEEE, 2008, 4 pages.
List of IBM Patents or Applications Treated as Related.
Non Final Office Action received for U.S. Appl. No. 16/880,021 dated Dec. 18, 2023, 74 pages.
Non Final Office Action received for U.S. Appl. No. 17/487,225 dated Feb. 1, 2024, 17 pages.
Office Action for U.S. Appl. No. 16/880,021 dated Jun. 17, 2024.
Duay, Searle S., et al. "Molecular dynamics investigation into the effect of zinc (II) on the structure and membrane interactions of the antimicrobial peptide clavanin A" The Journal of Physical Chemistry B 123.15 (2019): 3163-3176. (Year: 2019).
Rognan, Didier. "The impact of in silica screening in the discovery of novel and safer drug candidates." Pharmacology & therapeutics 175 (2017): 47-66. (Year: 2017).
Office Action for U.S. Appl. No. 17/487,225 dated May 23, 2024.
Ruangpan, Lila; "Minimual inhibitory concentration (mic) test and determination of antimicrobial resistant bacteria." Laboratory manual of standardized methods for antimicrobial sensitivity tests for bacteria isolated from aquatic animals and environment (2004) chapter 3, p. 31-55.
Sotos, Ana Elisa Castro et al., "The transitivity misconception of pearson's correlation coefficient." Statistical Ed. Res. (2009) 8(2) p. 33-55.

\* cited by examiner

TRANSFER LEARNING FOR MOLECULAR STRUCTURE GENERATION

BACKGROUND

The subject disclosure relates to the use of transfer learning to discover one or more molecular structures predicted to have desirable attributes, and more specifically, to the use of transfer learning with one or more machine learning models to generate molecular structures that are predicted to exhibit a defined attribute composition.

The discovery of novel chemical compounds having one or more desirable attribute profiles can be a tedious and time consuming endeavor. Artificial intelligence ("AI") technology has been employed to assist chemists in identifying molecular structures that characterize chemical compound candidates. However, the use of AI to conditionally generate novel materials is often impeded by a lack of training data regarding chemical compounds known to exhibit the desired trait. For instance, there may be few known chemical compounds that exhibit the attribute of interest, and even fewer where the desired attributes are known. Further, the scarcity of available training data can be exasperated when the desired chemical compound has a particular combination of attributes. Thus, conventional techniques that use AI to discover new chemical compounds for a particular context are impeded by a unique paradigm: the AI requires numerous examples of the type of chemical compound to train an accurate model; but if there were numerous examples readily available, the AI model may not be relevant.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatuses and/or computer program products that can autonomously discover molecular structures predicted to exhibit one or more desirable traits are described.

According to an embodiment, a system is provided. The system can comprise a memory that can store computer executable components. The system can also comprise a processor, operably coupled to the memory, and that can execute the computer executable components stored in the memory. The computer executable components can comprise a transfer learning component that determines a molecular structure of a compound by employing a transfer learning process that utilizes lessons learned from an unconditional generative machine learning model to train a conditional machine learning model that regards a target attribute profile. An advantage of such a system can be the generation of molecular structures having complex and particular attribute compositions of interest.

In some examples, the system can also comprise an encoder training component that can train the unconditional machine learning model by employing an autoencoder to analyze unlabeled data from a defined data distribution set. The unconditional machine learning model can be a neural network model, and the autoencoder can be an unconditional variational autoencoder. An advantage of such a system can be enhanced accuracy associated with the one or more machine learning models employed to generate the molecular structures.

According to an embodiment, a computer-implemented method is provided. The computer-implemented method can comprise determining, by a system operatively coupled to a processor, a molecular structure of a compound by employing a transfer learning process that utilizes lessons learned from an unconditional generative machine learning model to train a conditional machine learning model that regards a target attribute profile. An advantage of such a computer-implemented method can be the rapid generation of novel molecular structures by leveraging the computational capacity of machine learning.

In some examples, the computer-implemented method can further comprise training, by the system, the autoencoder with a regressor using a first training dataset that includes molecular structures of a first group of compounds that exhibit a first attribute. Also, the computer-implemented method can comprise training, by the system, autoencoder and regressor using a second training dataset that includes molecular structures of a second group of compounds that exhibit a second attribute. An advantage of such a computer-implemented method can be an enhanced accuracy in predicting whether a molecular structure will exhibit a target attribute profile despite limited training data regarding the particular attribute composition delineated in the profile.

According to an embodiment, a computer program product for autonomous discovery of a compound is provided. The computer program product can comprise a computer readable storage medium having program instructions embodied therewith. The program instructions can be executable by a processor to cause the processor to determine, by the processor, a molecular structure of a compound by employing a transfer learning process that utilizes lessons learned from an unconditional generative machine learning model to train a conditional machine learning model that regards a target attribute profile. An advantage of such a computer program product method can be the enabled use of machine learning models to render accurate predictions despite a lack of available training data.

In some examples, the program instructions can further cause the processor to train, by the processor, the autoencoder with a regressor using a first training dataset that includes molecular structures of a first group of compounds that exhibit a first attribute. Also, the program instructions can cause the processor to train, by the processor, autoencoder and regressor using a second training dataset that includes molecular structures of a second group of compounds that exhibit a second attribute. The target attribute profile comprises the first attribute and the second attribute. Additionally, the program instructions can cause the processor to train, by the processor, a classifier on a latent space learned by the autoencoder. Moreover, the program instructions can cause the processor to perform, by the processor, a conditional generation by executing the conditional machine learning model with rejection sampling in the latent space using a density model and the classifier. An advantage of such a computer program product method can be the generation of molecular structures that embody a defined combination of attributes of interest.

DETAILED DESCRIPTION

Figure 1:
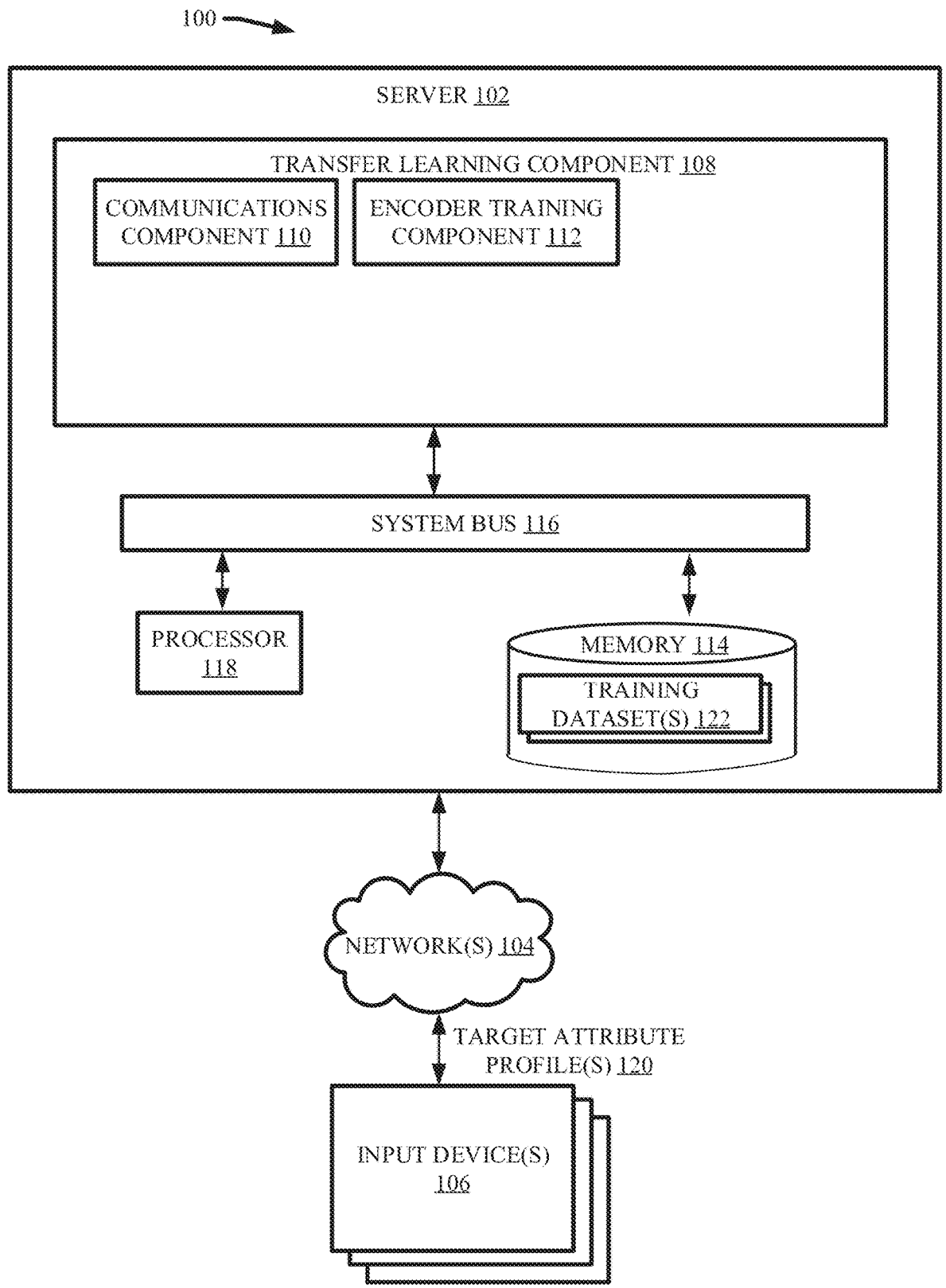
FIG. 1 illustrates a block diagram of an example, non-limiting system that can utilize transfer learning to employ one or more machine learning models and discover chemical compounds predicted to exhibit a desired attribute profile in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Given the problems with other implementations of chemical compound discovery techniques; the present disclosure can be implemented to produce a solution to one or more of these problems by utilizing transfer learning to generate machine learning models that can accurately predict chemical compounds with a desirable attribute profile. Advantageously, one or more embodiments described herein can train a machine learning model to determine molecular structures that are predicted to exhibit a particular attribute profile despite a considerable lack of training data regarding example chemical compounds that also exhibit the attribute profile.

Various embodiments of the present invention can be directed to computer processing systems, computer-implemented methods, apparatus and/or computer program products that facilitate the efficient, effective, and autonomous (e.g., without direct human guidance) determination of molecular structures that are predicted to exhibit a target attribute profile. For example, one or more embodiments described herein can utilize transfer learning to train one or more machine learning models on a variety of attribute datasets. For example, a first training dataset can include example molecular structures that exhibit a first attribute, while a second training dataset can include example molecular structures that exhibit a second attribute. The one or more machine learning models can be trained on both the first and second datasets by employing a transfer learning process so as to generate molecular structures predicted to exhibit an attribute profile that comprises both the first and second attributes. Thereby, the one or more machine learning models can generate the molecular structures in circumstances where there is a substantial lack of example chemical compounds having the attribute profile and available training data.

The computer processing systems, computer-implemented methods, apparatus and/or computer program products employ hardware and/or software to solve problems that are highly technical in nature (e.g., molecular structure determinations), that are not abstract and cannot be performed as a set of mental acts by a human. For example, an individual, or a plurality of individuals, cannot readily or efficiently analyze exemplary chemical compounds to determine one or more casual relationships between structural groups and attributes in an attempt to generate molecular structures predicted to exhibit a desirable attribute profile.

Also, one or more embodiments described herein can constitute a technical improvement over conventional chemical compound discovery techniques by utilizing transfer learning to enhance the accuracy of machine learning models despite a scarcity of training data. Additionally, various embodiments described herein can demonstrate a technical improvement over conventional chemical compound discovery techniques by implementing lessons learned from analyzing chemical compounds having alternate attribute profiles to generate novel chemical compounds having a desirable attribute profile. For example, various embodiments described herein can determine one or more molecular structures predicted to exhibit a target attribute profile despite a lack of example chemical compounds known to exhibit the target attribute profile.

Further, one or more embodiments described herein can have a practical application by enabling the generation of novel chemical compounds that exhibit attributes targeted for a particular context and/or function. For instance, various embodiments described herein can be employed to generate one or more therapeutic compounds having an attribute profile characterized by one or more size constraints and/or desired binding affinities. One or more embodiments described herein can control one or more neural networks to implement transfer learning that trains one or more machine learning models. Thereby, the one or more embodiments, can apply machine learned lessons derived from various contexts to supplement a lack of chemical compound training data.

As used herein, the term "machine learning" can refer to an application of AI technologies to automatically and/or autonomously learn and/or improve from an experience (e.g., training data) without explicit programming of the lesson learned and/or improved. For example, machine learning can utilize one or more algorithms to facilitate supervised and/or unsupervised learning to perform tasks such as classification, regression, and/or clustering. Execution of a machine learning can be facilitated by one or more artificial intelligence models trained on one or more datasets in accordance with one or more model configuration settings.

As used herein, the terms "machine learning model" and/or "machine learning models" can refer to a computer model that can be used to facilitate machine learning, wherein the computer model can simulate a number of interconnected processing units that can resemble abstract versions of neurons. For example, the one or more machine learning models described herein can include neural network models that include processing units arranged in a plurality of layers (e.g., one or more input layers, one or more hidden layers, and/or one or more output layers) connected with by varying connection strengths (e.g., which can be commonly referred to within the art as "weights"). Neural network models can learn through training, wherein data with known outcomes is inputted into the computer model, outputs regarding the data are compared to the known outcomes, and/or the weights of the computer model are autonomous adjusted based on the comparison to replicate the known outcomes. As used herein, the term "training dataset" can refer to data and/or data sets used to train one or more machine learning models, such as neural network models. As a machine learning model (e.g., a neural network model) trains (e.g., utilizes more training data), the computer model can become increasingly accurate; thus, trained machine learning models (e.g., neural network models) can accurately analyze data with unknown outcomes, based on lessons learning from training datasets, to facilitate one or more machine learning tasks. Example neural network models can include, but are not limited to: perceptron ("P"), feed forward ("FF"), radial basis network ("RBF"), deep feed forward ("DFF"), recurrent neural network ("RNN"), long/short term memory ("LSTM"), gated recurrent unit ("GRU"), auto encoder ("AE"), variational AE ("VAE"), denoising AE ("DAE"), sparse AE ("SAE"), markov chain ("MC"), Hopfield network ("HN"), Boltzmann machine ("BM"), deep belief network ("DBN"), deep convolutional network ("DCN"), deconvolutional network ("DN"), deep convolutional inverse graphics network ("DCIGN"), generative adversarial network ("GAN"), liquid state machine ("LSM"), extreme learning machine ("ELM"), echo state network ("ESN"), deep residual network ("DRN"), kohonen network ("KN"), support vector machine ("SVM"), and/or neural turing machine ("NTM").

FIG. 1 illustrates a block diagram of an example, non-limiting system 100 that can generate one or more molecular structures predicted to exhibit a target attribute profile. Repetitive description of like elements employed in other embodiments described herein is omitted for sake of brevity. Aspects of systems (e.g., system 100 and the like), apparatuses or processes in various embodiments of the present invention can constitute one or more machine-executable components embodied within one or more machines, e.g., embodied in one or more computer readable mediums (or media) associated with one or more machines. Such components, when executed by the one or more machines, e.g., computers, computing devices, virtual machines, etc. can cause the machines to perform the operations described.

As shown in FIG. 1, the system 100 can comprise one or more servers 102, one or more networks 104, and/or input devices 106. The server 102 can comprise transfer learning component 108. The transferring learning component 108 can further comprise communications component 110 and encoder training component 112. Also, the server 102 can comprise or otherwise be associated with at least one memory 114. The server 102 can further comprise a system bus 116 that can couple to various components such as, but not limited to, the transfer learning component 108 and associated components, memory 114 and/or a processor 118. While a server 102 is illustrated in FIG. 1, in other embodiments, multiple devices of various types can be associated with or comprise the features shown in FIG. 1. Further, the server 102 can communicate with one or more cloud computing environments.

The one or more networks 104 can comprise wired and wireless networks, including, but not limited to, a cellular network, a wide area network (WAN) (e.g., the Internet) or a local area network (LAN). For example, the server 102 can communicate with the one or more input devices 106 (and vice versa) using virtually any desired wired or wireless technology including for example, but not limited to: cellular, WAN, wireless fidelity (Wi-Fi), Wi-Max, WLAN, Bluetooth technology, a combination thereof, and/or the like. Further, although in the embodiment shown the transfer learning component 108 can be provided on the one or more servers 102, it should be appreciated that the architecture of system 100 is not so limited. For example, the transfer learning component 108, or one or more components of transfer learning component 108, can be located at another computer device, such as another server device, a client device, etc.

The one or more input devices 106 can comprise one or more computerized devices, which can include, but are not limited to: personal computers, desktop computers, laptop computers, cellular telephones (e.g., smart phones), computerized tablets (e.g., comprising a processor), smart watches, keyboards, touch screens, mice, a combination thereof, and/or the like. The one or more input devices 106 can be employed to enter one or more target attribute profiles 120 and/or training datasets 122 into the system 100, thereby sharing (e.g., via a direct connection and/or via the one or more networks 104) said data with the server 102. For example, the one or more input devices 106 can send data to the communications component 110 (e.g., via a direct connection and/or via the one or more networks 104). Additionally, the one or more input devices 106 can comprise one or more displays that can present one or more outputs generated by the system 100 to a user. For example, the one or more displays can include, but are not limited to: cathode tube display ("CRT"), light-emitting diode display ("LED"), electroluminescent display ("ELD"), plasma display panel ("PDP"), liquid crystal display ("LCD"), organic light-emitting diode display ("OLED"), a combination thereof, and/or the like.

In various embodiments, the one or more input devices 106 and/or the one or more networks 104 can be employed to input one or more settings and/or commands into the system 100. For example, in the various embodiments described herein, the one or more input devices 106 can be employed to operate and/or manipulate the server 102 and/or associate components. Additionally, the one or more input devices 106 can be employed to display one or more outputs (e.g., displays, data, visualizations, and/or the like) generated by the server 102 and/or associate components. Further, in one or more embodiments, the one or more input devices 106 can be comprised within, and/or operably coupled to, a cloud computing environment.

In one or more embodiments, the one or more input devices 106 can be employed to enter one or more target attribute profiles 120 into the system 100. Further, the one or more input devices 106 can utilize the one or more networks 104 and/or direct electrical connections to share the one or more target attribute profiles 120 with the transfer learning component 108 (e.g., via communications component 110). For example, the communications component 110 can receive one or more entries of the input devices (e.g., target attribute profiles 120) and share the entries with various associate components of the transfer learning component 108. The one or more target attribute profiles 120 can delineate one or more desirable attributes to be exhibited by the molecular structures generated by the transfer learning component 108 in accordance with various embodiments described herein. In various embodiments, the one or more target attribute profiles 120 can delineate a single desirable attribute or a composition of multiple desirable attributes.

Example physical and/or chemical attributes that can be delineated within the one or more target attribute profiles 120 can include, but are not limited to: molecular size, molecular composition, molecular binding sites, molecular binding affinities, chemical reactivity, acidity, electrical charge (e.g., cationic or anionic complexes), toxicity, antimicrobial activity, protein sequencing, polarity, hydrophobicity, hydrophilicity, solubility, medication-likeness, molecular weight, a combination thereof, and/or the like. Additionally, the one or more target attribute profiles 120 can regard how the generated molecular structures are synthesized, including, but not limited to: available starting materials, types of synthesis reactions employed (e.g., ring-opening polymerizations, batch reaction processing, flow reaction processing, and/or the like), catalysts required for synthesis, synthesis completion times, various quantitative measures of synthetic accessibility, number of reaction steps needed for synthesis, a combination thereof, and/or the like.

Additionally, the one or more input devices 106 can be employed to enter one or more training datasets 122 into the system 100. For example, the one or more training datasets 122 can be stored in the one or more memories 114. The transfer learning component 108 can utilize the one or more training datasets 122 to train one or more machine learning models to generate molecular structures associated with the one or more target attribute profiles 120 in accordance with the various embodiments described herein. In various embodiments, each training dataset 122 can regard a respective attribute that can be comprised within the one or more target attribute profiles 120. For example, each training dataset 122 can include a group of example molecular structures that exhibit an attribute. For instance, a first training dataset 122 can include a group of example molecular structures that exhibit a first attribute, while a second training dataset 122 can include a group of example molecular structures that exhibit a second attribute. In one or more embodiments, each of the attributes comprised in the one or more target attribute profiles 120 can be associated with at least one training dataset 122. In various embodiments, the system 100 can lack access to training data regarding a particular attribute, but can estimate the property computationally using the training datasets 122 for other attributes.

In various embodiments, the encoder training component 112 can train an unconditional machine learning model by employing one or more autoencoders to analyze unlabeled data from a defined data distribution set. For example, the one or more autoencoders can be one or more unconditional variational autoencoders comprised within a neural network model, such as a bidirectional regional neural network. Additionally, the encoder training component 112 can train one or more decoders on the unlabeled data. For example, the defined data distribution set can characterize the molecular structures for a defined group of chemical compounds. The encoder training component 112 can supply the molecular structures to the one or more autoencoders to encode one or more latent representations, which can then be decoded by the one or more decoders to reconstruct the molecular structures. The encoder training component 112 can analyze the latent representations to determine one or more Kullback-Leibler divergence values ("KL-loss"). Additionally, the encoder training component 112 can compare the reconstructed molecular structures with the supplied molecular structures to determine one or more reconstruction loss values. Moreover, in various embodiments the encoder training component 112 can analyze the latent representations to determine one or more classification and/or regression loss values regarding one or more attributes attributed to the molecular structures. Based on the KL-loss, reconstruction loss, and/or classification/regression loss values, the encoder training component 112 can determine whether the one or more autoencoders and/or decoders are pre-trained for subsequent transfer learning procedures described herein. For example, the encoder training component 112 can compare the one or more KL-loss, reconstruction loss, and/or classification/regression loss values to one or more defined thresholds to facilitate the determinations.

Figure 2:
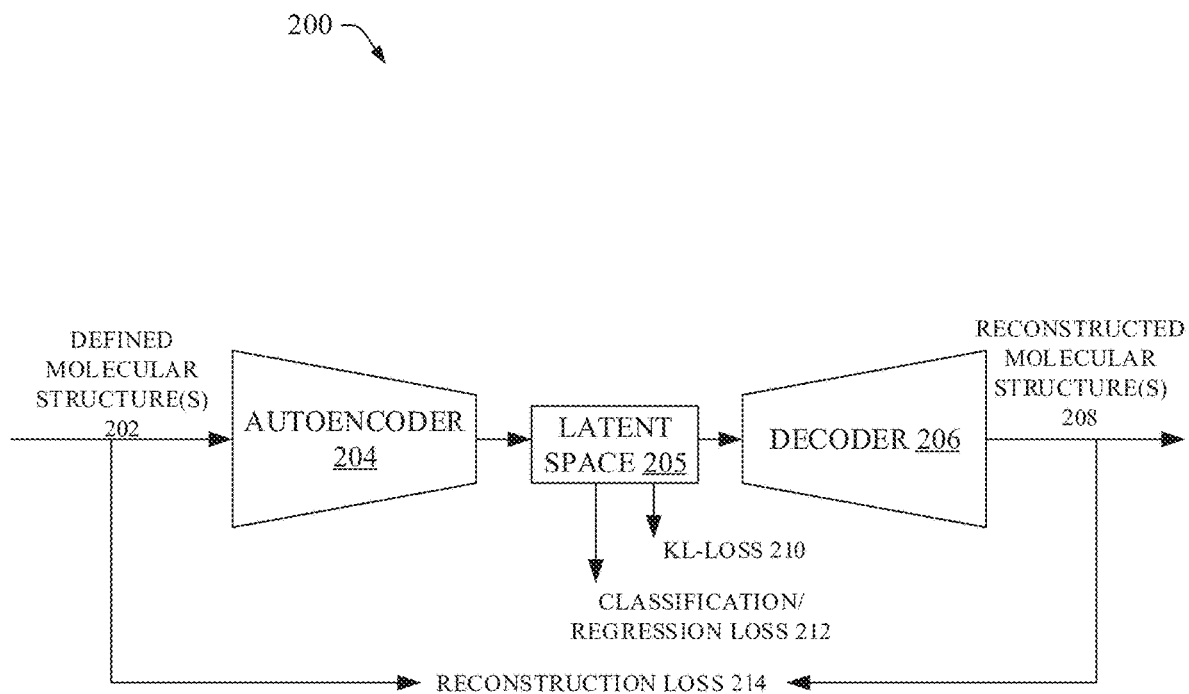
FIG. 2 illustrates a diagram of an example, non-limiting training procedure that can be implemented to train one or more autoencoders of a machine learning model to facilitate discovery of chemical compounds predicted to exhibit a desired attribute profile in accordance with one or more embodiments described herein.

FIG. 2 illustrates a diagram of an example, non-limiting variational autoencoder training process 200 that can be implemented by the encoder training component 112 in accordance with one or more embodiments described herein. Repetitive description of like elements employed in other embodiments described herein is omitted for sake of brevity.

As shown in FIG. 2, the encoder training component 112 can supply one or more defined molecular structures 202 to one or more autoencoders 204. For example, the encoder training component 112 can retrieve the one or more defined molecular structure 202 from the one or more memories 114, such as from one or more training datasets 122. The one or more autoencoders 204 can be variational autoencoders that encode latent representations of the defined molecular structures 202 to a latent space 205, as described herein. Further, the latent space 205 can be decoded by one or more decoders 206 to generated one or more reconstructed molecular structures 208. Also shown in FIG. 2, the encoder training component 112 can analyze the representations included in the latent space 205 to determine KL-loss 210 and/or classification/regression loss 212. Further, the encoder training component can compare the reconstructed molecular structures 208 and the defined molecular structures 202 to determine reconstruction loss 214.

Figure 3:
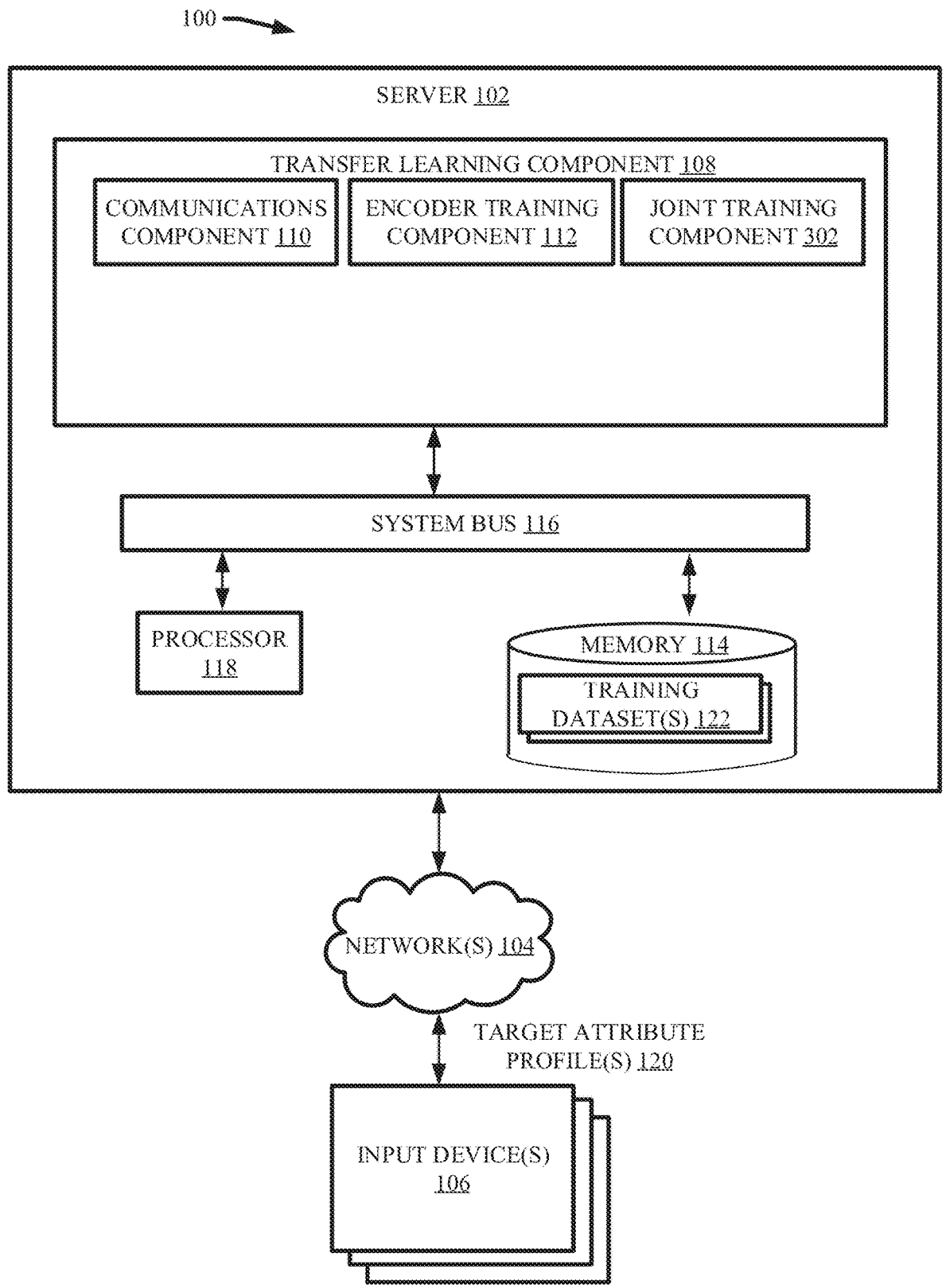
FIG. 3 illustrates a block diagram of the example, non-limiting system that can utilize lessons learned form a first training dataset to facilitate training a machine learning model on a second training dataset in accordance with one or more embodiments described herein.

FIG. 3 illustrates a diagram of the example, non-limiting system 100 further comprising joint training component 302 in accordance with various embodiments described herein. Repetitive description of like elements employed in other embodiments described herein is omitted for sake of brevity. In various embodiments, the joint training component 302 can jointly train the unconditional machine learning model with a conditional machine learning model.

In various embodiments, the joint training component 302 can further train the one or more autoencoders 204 (e.g., variational autoencoders) with one or more regressors and/or classifiers using a first training dataset. For example, the first training dataset 122 can include example molecular structures associated with a first attribute. Additionally, in one or more embodiments the first training dataset 122 can have the most molecular structure examples amongst the available training datasets 122. Thereby, the joint training component 302 can train the one or more autoencoders 204, regressors, and/or classifiers to predict the first attribute. For example, the joint training component 302 can utilize the first training dataset 122 to assist the autoencoders 204 (e.g., variational autoencoders) to learn a disentangled latent space 205 that can accurately predict whether a molecular structure exhibits the first attribute.

Subsequently, the joint training component 302 can further train the one or more autoencoders 204 (e.g., variational autoencoders) with one or more additional regressors and/or classifiers using one or more additional training datasets 122. For example, the joint training component 302 can further train the one or more autoencoders 204 (e.g., variational autoencoders) with one or more second regressors and/or classifiers using a second training dataset 122. For instance, the second training dataset 122 can include example molecular structures associated with a second attribute. Thereby, the joint training component 302 can train the one or more autoencoders 204, regressors, and/or classifiers to predict the second attribute. In various embodiments, the joint training component 302 can continue to train the one or more autoencoders 204 (e.g., variational autoencoders) with additional regressors and/or classifiers on each of the training datasets 122, and thereby each of the attributes associated with the training datasets 122. By analyzing each training dataset 122 the transfer learning component 108 can apply lessons learned from training directed to a first attribute to training directed to additional attributes.

Figure 4:
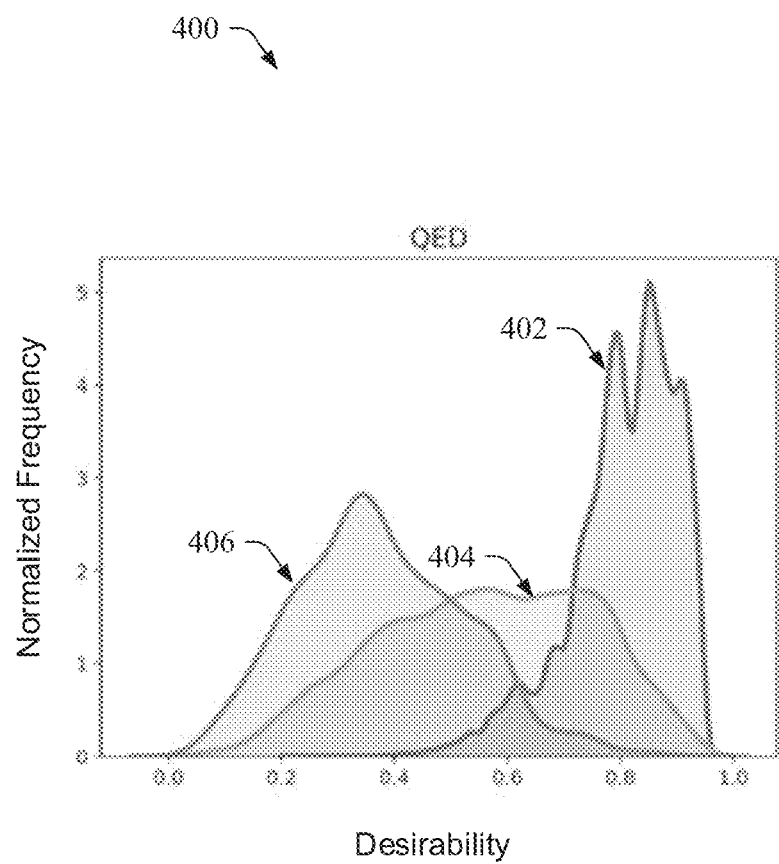
FIG. 4 illustrates a diagram of an example, non-limiting graph that can characterize three exemplary datasets that can be used to exemplify various features of a system that can utilize transfer learning to employ one or more machine learning models and discover chemical compounds predicted to exhibit a desired attribute profile in accordance with one or more embodiments described herein.

FIG. 4 illustrates a diagram of an example, non-limiting graph 400 regarding exemplary training datasets 122 that can be analyzed by the joint training component 302 in accordance with one or more embodiments described herein. Repetitive description of like elements employed in other embodiments described herein is omitted for sake of brevity. For example, the system 100 can be employed to generate molecular structures for one or more therapeutic compounds. Graph 400 can characterize the distribution of quantitative estimate of medication-likeness ("QED") with respect to an exemplary use case scenario regarding a target attribute profile 120 that delineates the following three attributes: small molecules size (e.g., having a molecular weight of less than 500 molar mass ("M"); high bonding affinity (e.g., having a pIC50 value of greater than 6); and histone deacetylase 1 ("HDAC1") targeting.

As shown in graph 400, the first line 402 can characterize a first training dataset 122 that includes molecular structures from the ZINC small molecule database. The second line 404 can characterize a second training dataset 122 that includes molecular structures from the BindingDB binding affinities database. The third line 406 can characterize a third training dataset 122 that include molecular structures that bind to HDAC1 in accordance with the BindingDB database. Graph 400 illustrates that QED can be high for small molecules of the first training dataset 122, but low for high bonding affinity molecules of the second training dataset 122 and HDAC1 targeting molecules of the third training dataset 122. In particular, the QED distribution exemplifies the scarcity of training examples that meeting all three attributes of the target attribute profile 120.

The three training datasets 122 characterized by graph 400 can be analyzed by the system 100 to train the one or more autoencoders 204 (e.g., variational autoencoders) to predict whether a molecular structure meets the target attribute profile 120. For example, the encoder training component 112 can performed unsupervised training of the one or more autoencoders 204 (e.g., variational autoencoders) with a regional neural network on a defined distribution set from the first training dataset. The joint training component 302 can subsequently further train the one or more autoencoders 204 (e.g., variational autoencoders) with one or more regressors and/or classifiers on the small molecules of the first training dataset 122. For example, the joint training component 302 can further train the one or more autoencoders 204 (e.g., variational autoencoders) with two regressors and/or classifiers regarding molecular properties of the molecules (e.g., such as a first regressor and/or classifier regarding QED and/or a second regressor and/or classifier regarding synthetic accessibility). Thereafter, the joint training component 302 can further train the one or more autoencoders 204 (e.g., variational autoencoders) with the one or more regressors and/or classifiers on the binding affinity molecules of the second training dataset 122. Moreover, the joint training component 302 can train the one or more autoencoders 204 (e.g., variational autoencoders) with one or more regressors and/or classifiers on the HDAC1 targeting molecules of the third training dataset 122.

Figure 5:
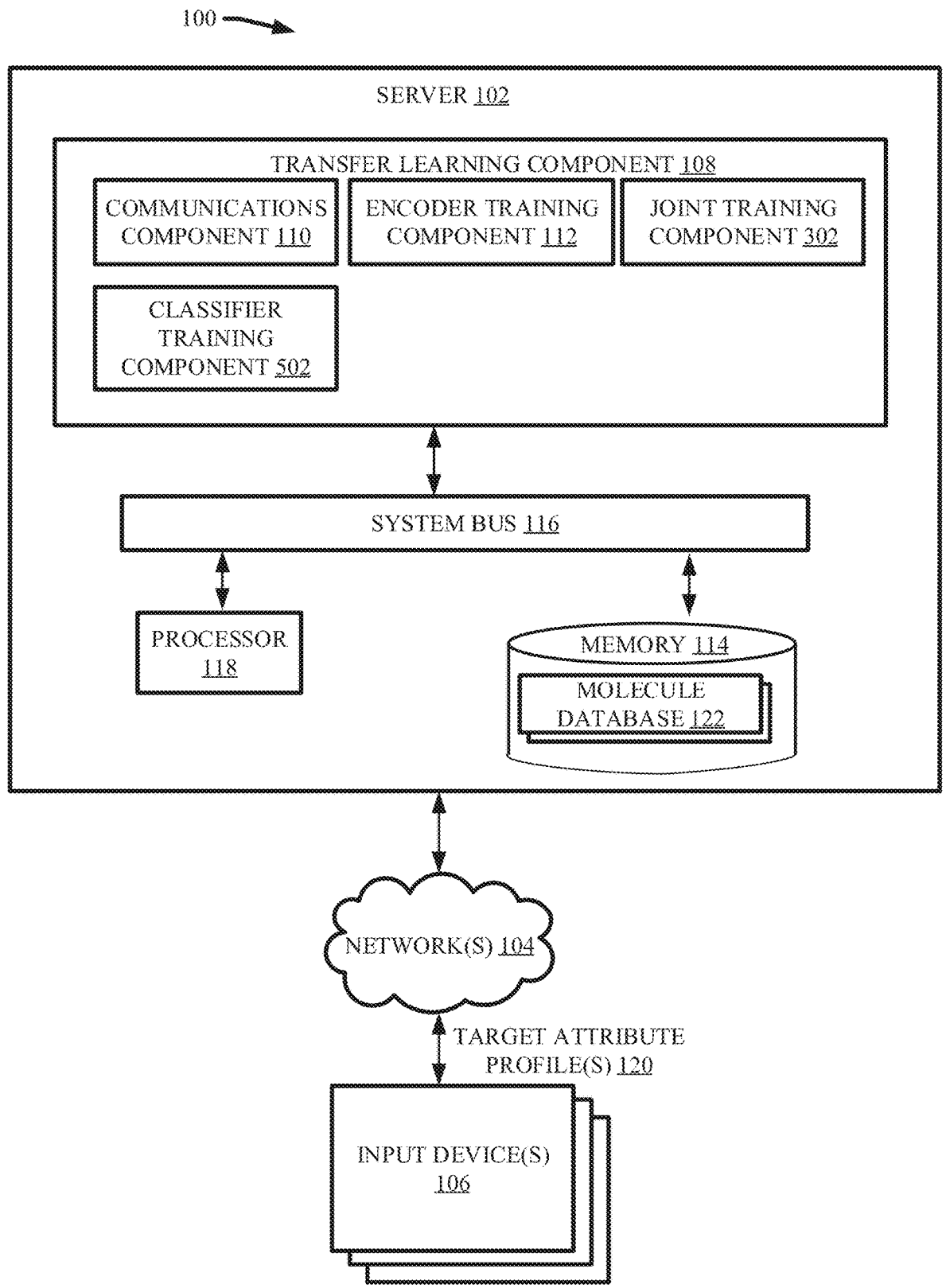
FIG. 5 illustrates a block diagram of the example, non-limiting system that can train one or more classifiers of a machine learning model in a latent space trained on multiple datasets regarding chemical compounds have attributes comprised within a desired attribute profile in accordance with one or more embodiments described herein.

FIG. 5 illustrates a diagram of the example, non-limiting system 100 further comprising classifier training component 502 in accordance with one or more embodiments described herein. Repetitive description of like elements employed in other embodiments described herein is omitted for sake of brevity. In various embodiments, the classifier training component 502 can train one or more classifiers on the latent space 205 learned by the one or more autoencoders 204. Thereby, the classifier component 502 can train the one or more classifiers on those attributes for which the one or more training datasets 122 comprises limited training data.

For example, with reference to the exemplary use case scenario described above with regards to FIG. 4, the classifier training component 502 can train two or more classifiers on the learned latent space 205 encoded by the one or more autoencoders 204 (e.g., variational autoencoders) to predict a QED value for a generated molecular structure and/or the generated molecular structure's binding affinity towards the HDAC1 target.

Figure 6:
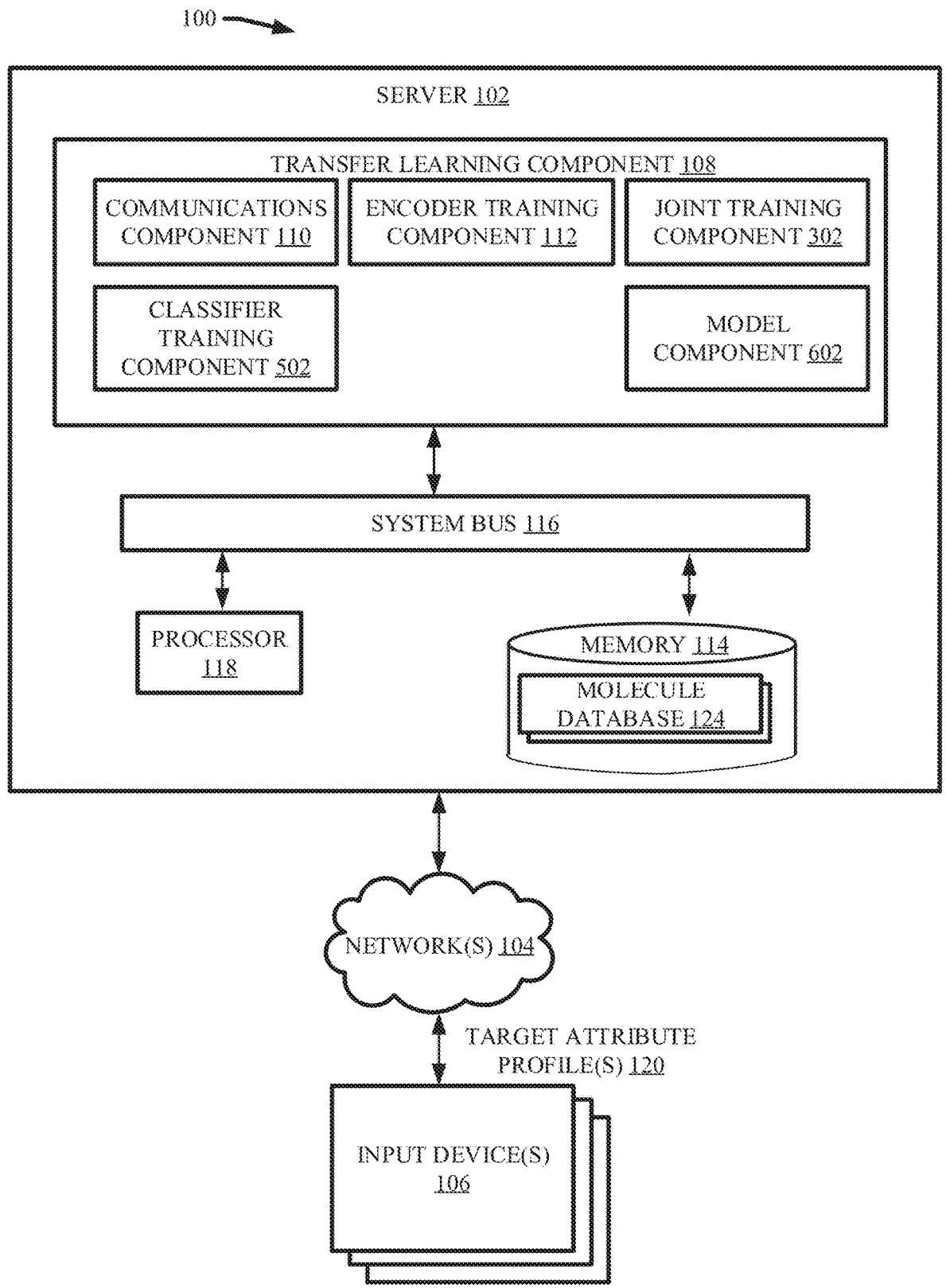
FIG. 6 illustrates a block diagram of the example, non-limiting system that can perform conditional generating by executing a conditional machine learning model with rejection sampling in accordance with one or more embodiments described herein.

FIG. 6 illustrates a diagram of the example, non-limiting system 100 further comprising model component 602 in accordance with one or more embodiments described herein. Repetitive description of like elements employed in other embodiments described herein is omitted for sake of brevity. In various embodiments, the model component 602 can perform conditional generation of one or more molecular structures by executing a conditional machine learning model with conditional sampling (e.g., rejection sampling)

in the latent space 205 using one or more density models and the one or more trained classifiers.

For example, the model component 602 can employ the trained classifiers to perform one or more Monte Carlo sampling techniques, such as rejection sampling. Further the model component 602 can fit a density model on the z-space of the latent representations (e.g., via a mixture of gaussian determinations). In one or more embodiments, the model component 602 can perform rejection sampling using a plurality of trained classifiers and the one or more density models. For example, one or more rejection/acceptance criteria can be derived from the one or more trained classifiers based on the given target attribute profile 122 and lessons learned during the training performed by the joint training component 302.

In various embodiments the model component 602 can generate and/or fit one or more density models to the latent space 205 based on the one or more target attribute profiles 122. The one or more density models can be statistical models employed by the model component 602 to compute an underlying probability associated with the generated molecular structures having the target attribute profile 122. In various embodiments, the one or more density models can be mixture models and/or Gaussian mixture models. For instance, the one or more Gaussian mixture models can be extended to fit a vector of the attributes comprised within the one or more target attribute profiles 122 and/or multivariate normal distribution.

Figure 7:
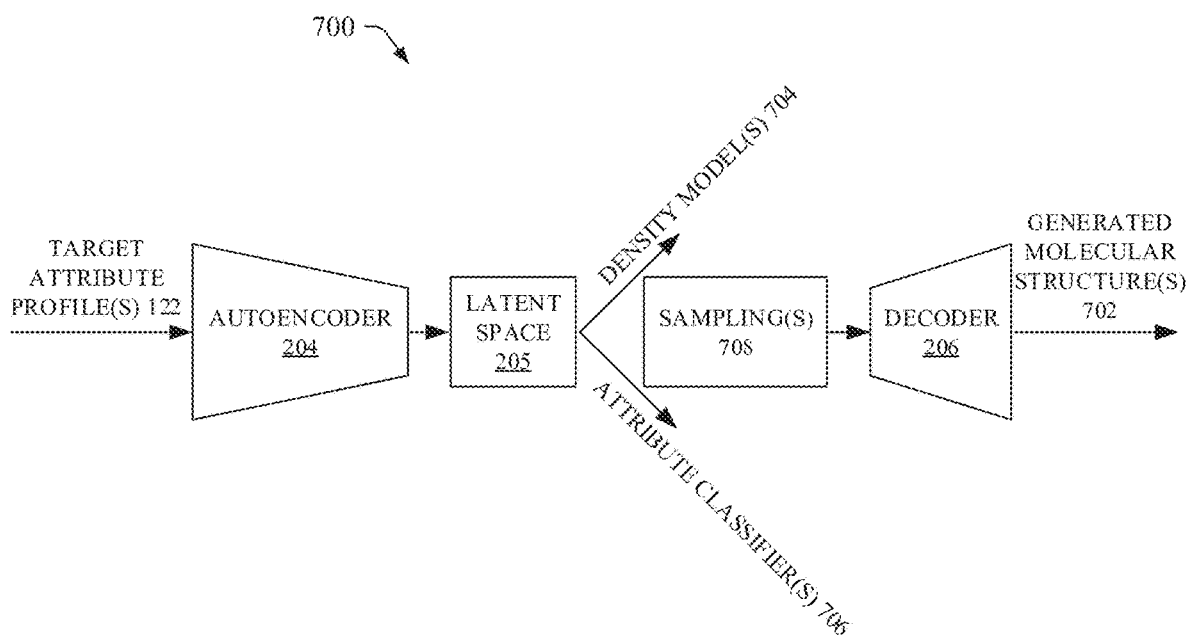
FIG. 7 illustrates a diagram of an example, non-limiting conditional generation procedure that can be implemented by one or more machine learning models to facilitate discovery of chemical compounds predicted to exhibit a desired attribute profile in accordance with one or more embodiments described herein.

FIG. 7 illustrates a diagram of an example, non-limiting conditional generation procedure 700 that can be implemented by the model component 602 in accordance with one or more embodiments described herein. Repetitive description of like elements employed in other embodiments described herein is omitted for sake of brevity. As shown in FIG. 7, the conditional generation procedure 700 can receive one or more target attribute profiles 122 (e.g., via one or more input devices 106 and/or networks 104) to direct computation of one or more generated molecular structures 702 that are predicted to exhibit attributes of interest.

In accordance with the various embodiments described herein, the one or more autoencoders 204 (e.g., variational autoencoders) can be trained on a plurality of training datasets 122 regarding molecule examples exhibiting respective attributes. Thereby, one or more autoencoders 204 (e.g., variational autoencoders) can encode latent representations to the latent space 205. Further, the model component 602 can fit one or more density models 704 to the latent space 205 regarding the one or more target attribute profiles 122. Additionally, in accordance with the various embodiments described herein, the classifier component 502 can train one or more attribute classifiers 706 in the latent space 205 for one or more attributes of the one or more target attribute profiles 122. Further, the model component 602 can employ the one or more density models 704 and/or attribute classifiers 706 to perform one or more samplings 708. For example, the one or more samplings 708 can be one or more conditional sampling techniques, such as a Monte Carlo sampling technique (e.g., rejection sampling). Thereby, the transfer learning component 108 can compute one or more generated molecular structures 702 that are predicted to exhibit the target attribute profile 122 based on lessons learned across a plurality of training datasets 122 that can regard individual attributes but not necessarily the particular attribute composition delineated by the target attribute profile 122.

Figure 8:
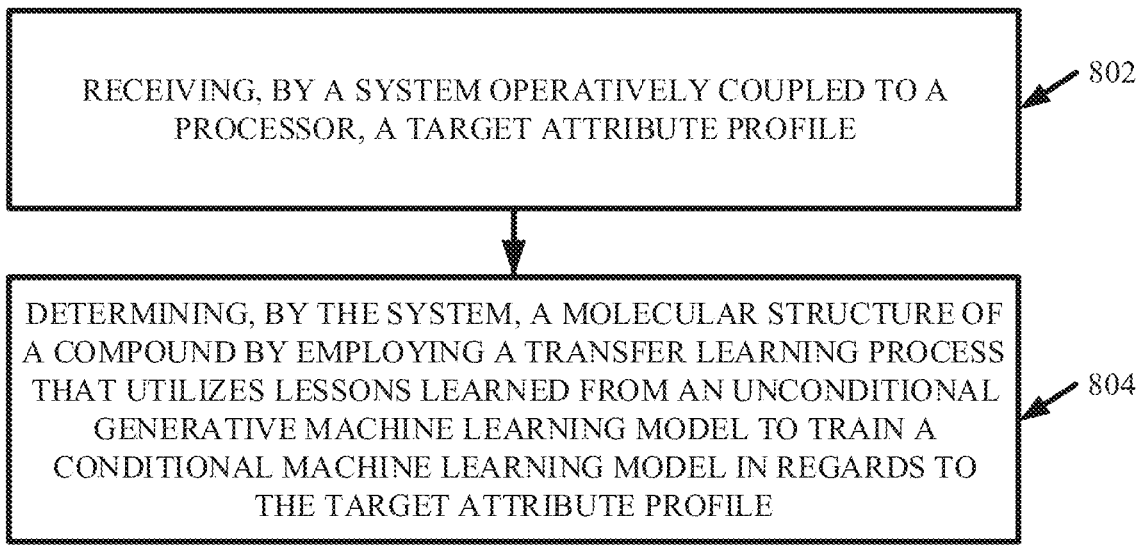
FIG. 8 illustrates a flow diagram of an example, non-limiting computer-implemented method that can facilitate using transfer learning to employ one or more machine learning models and discover chemical compounds predicted to exhibit a desired attribute profile in accordance with one or more embodiments described herein.

FIG. 8 illustrates a flow diagram of an example, non-limiting computer-implemented method 800 that can facilitate generating molecular structures that exhibit one or more attributes of interest in accordance with one or more embodiments described herein. Repetitive description of like elements employed in other embodiments described herein is omitted for sake of brevity.

At 802, the computer-implemented method 800 can comprise receiving (e.g., via communications component 110), by a system 100 operatively coupled to a processor 118, one or more target attribute profiles 122. For example, the one or more target attribute profiles 122 can delineate one or more attributes of interest considered desirable for one or more molecular structures generated by the system 100 in accordance with the various embodiments described herein. For instance, the one or more target attribute profiles 122 can delineate one or more physical properties, chemical properties, and/or conditions of synthesis regarding the to be generated molecular structures.

At 804, the computer-implemented method 800 can comprise determining (e.g., via transfer learning component 108), by the system 100, one or more molecular structures of a compound (e.g., a therapeutic compound) by employing one or more transfer learning processes that utilize lessons learned from an unconditional generative machine learning model to train a conditional machine learning model in regards to the one or more target attribute profiles 122. For example, determining at 804 can include one or more autoencoders 204 (e.g., variational autoencoders), regressors, and/or classifiers (e.g., attribute classifiers 706) of a machine learning model on a plurality of training datasets 122. Further, the determining at 804 can include employing the trained autoencoders 204 (e.g., variational autoencoders) and/or classifiers (e.g., attribute classifiers 706) with one or more density models 704 to perform conditional sampling (e.g., rejection sampling) that can accurately predict the occurrence of the target attribute profile 122.

Figure 9:
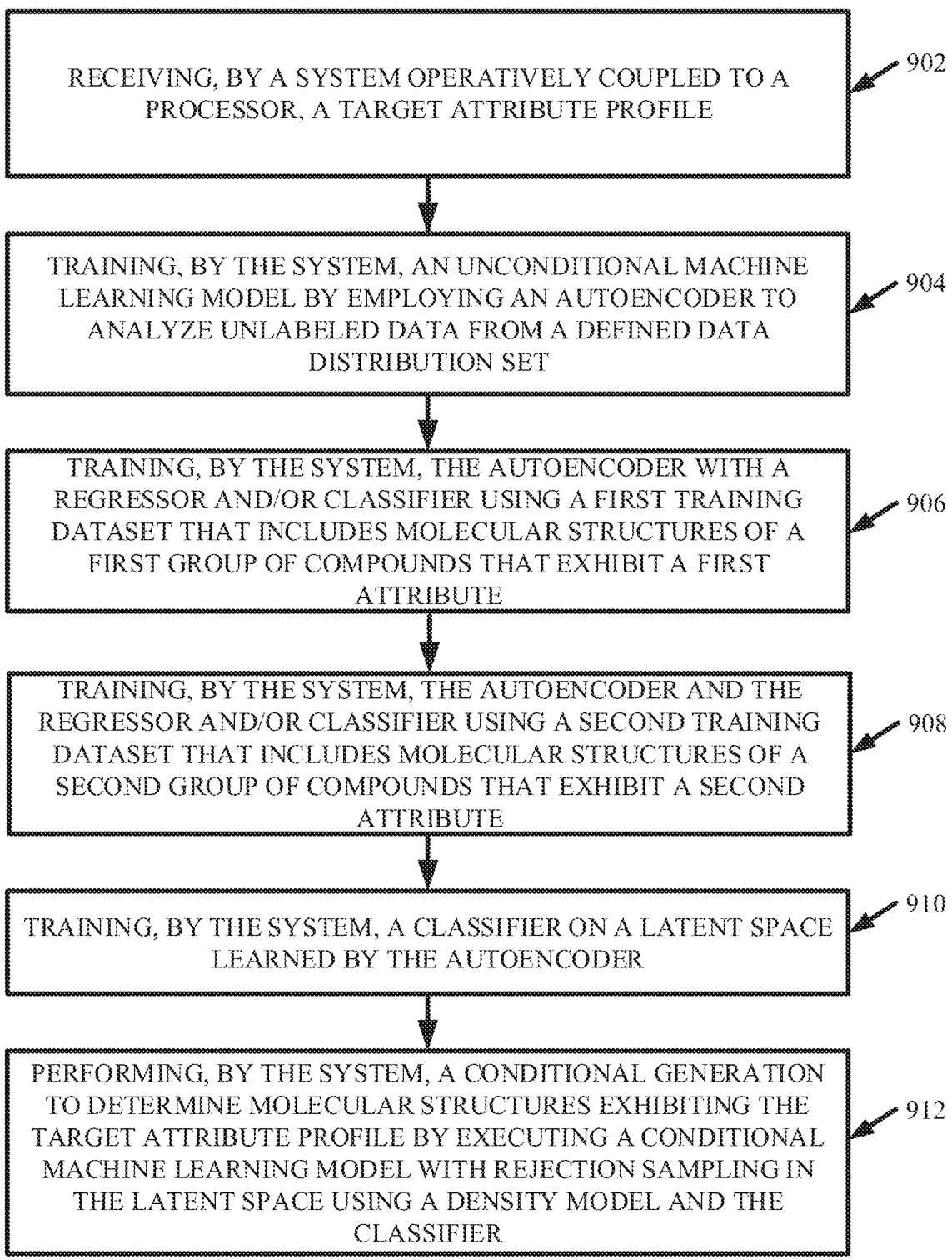
FIG. 9 illustrates a flow diagram of an example, non-limiting computer-implemented method that can facilitate using transfer learning to employ one or more machine learning models and discover chemical compounds predicted to exhibit a desired attribute profile in accordance with one or more embodiments described herein.

FIG. 9 illustrates a flow diagram of an example, non-limiting computer-implemented method 900 that can facilitate generating molecular structures that exhibit one or more attributes of interest in accordance with one or more embodiments described herein. Repetitive description of like elements employed in other embodiments described herein is omitted for sake of brevity.

At 902, the computer-implemented method 900 can comprise receiving (e.g., via communications component 110), by a system 100 operatively coupled to a processor 118, one or more target attribute profiles 122. For example, the one or more target attribute profiles 122 can delineate one or more attributes of interest considered desirable for one or more molecular structures generated by the system 100 in accordance with the various embodiments described herein. For instance, the one or more target attribute profiles 122 can delineate one or more physical properties, chemical properties, and/or conditions of synthesis regarding the to be generated molecular structures.

At 904, the computer-implemented method 900 can comprise training (e.g., via encoder training component 112), by the system 100, one or more unconditional machine learning models by employing one or more autoencoders 204 (e.g., variational autoencoders) to analyze unlabeled data from a defined data distribution set. For example, the training at 904 can include computing KL-loss 210, classification/regression loss 212, and/or reconstruction loss 214 in accordance with various embodiments described herein.

At 906, the computer-implemented method 900 can comprise training (e.g., via joint training component 302), by the system 100, the one or more autoencoders 204 (e.g., variational autoencoders) with one or more regressors and/or classifiers using a first training dataset 122 that can include one or more molecular structures of a first group of compounds that exhibit a first attribute. At 908, the computer-implemented method 900 can further comprise training (e.g., via joint training component 302), by the system 100, the one or more autoencoders 204 (e.g., variational autoencoders) and regressors and/or classifiers using a second training dataset 122 that can include one or more molecular structures of a second group of compounds that exhibit a second attribute. In various embodiments, the first and second attributes can be included within the target attribute profile 122 received at 902. For instance, graph 400 depicts an exemplification of multiple training datasets 122, each regarding a particular attribute, that can be utilized to train the one or more autoencoders 204 in accordance with the features of 906 and 908 and the various embodiments described herein.

At 910, the computer-implemented method 900 can comprise training (e.g., via classifier training component 502), by the system 100, one or more classifiers (e.g., attribute classifiers 706) on a latent space 205 learned by the one or more autoencoders 204. Further, at 912 the computer-implemented method 900 can comprise performing (e.g., via model component 602), by the system 100, one or more conditional generations to determine molecular structures exhibiting the target attribute profile 122 by executing a conditional machine learning model with rejection sampling in the latent space 205 using a density model (e.g., density model 704) and the one or more classifiers (e.g., attribute classifiers 706) in accordance with various embodiments described herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 10:
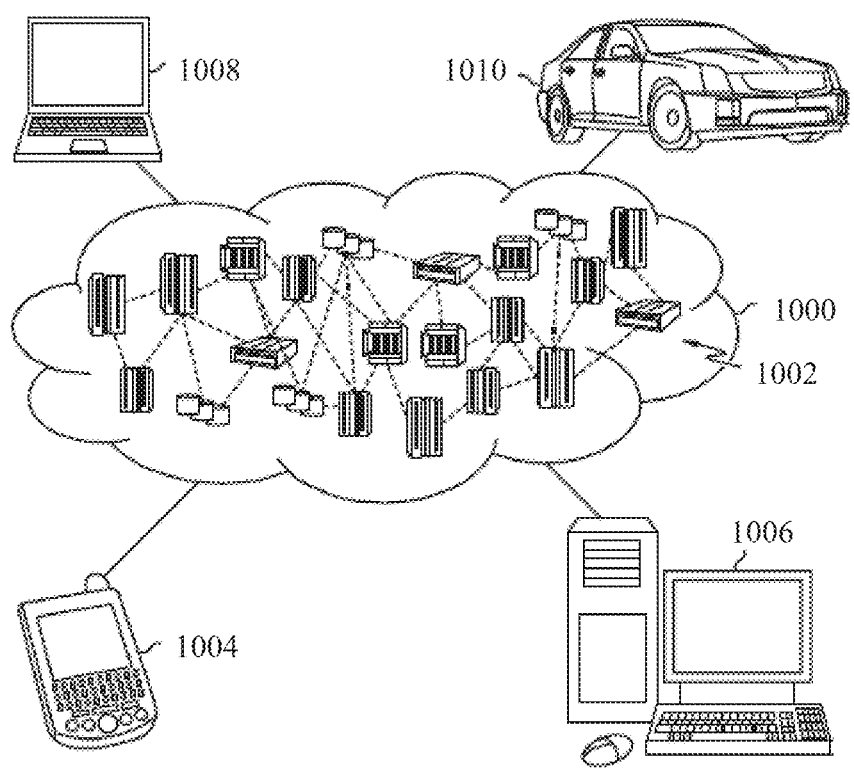
FIG. 10 depicts a cloud computing environment in accordance with one or more embodiments described herein.

Referring now to FIG. 10, illustrative cloud computing environment 1000 is depicted. As shown, cloud computing environment 1000 includes one or more cloud computing nodes 1002 with which local computing devices used by cloud consumers, such as, for example, personal digital assistant (PDA) or cellular telephone 1004, desktop computer 1006, laptop computer 1008, and/or automobile computer system 1010 may communicate. Nodes 1002 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1004-1010 shown in FIG. 10 are intended to be illustrative only and that computing nodes 1002 and cloud computing environment 1000 can communicate with any type of computerized device over any type of network and/or network addressable connection (e.g., using a web browser).

Figure 11:
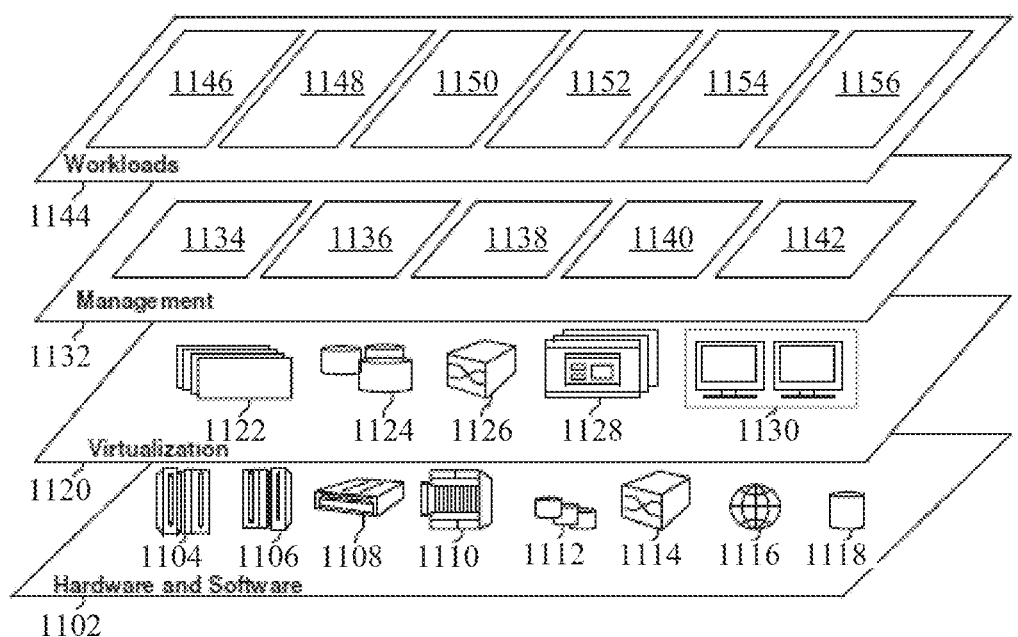
FIG. 11 depicts abstraction model layers in accordance with one or more embodiments described herein

Referring now to FIG. 11, a set of functional abstraction layers provided by cloud computing environment 1000 (FIG. 10) is shown. Repetitive description of like elements employed in other embodiments described herein is omitted for sake of brevity. It should be understood in advance that the components, layers, and functions shown in FIG. 11 are intended to be illustrative only and embodiments of the invention are not limited thereto. As depicted, the following layers and corresponding functions are provided.

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and transfer learning 1156. Various embodiments of the present invention can utilize the cloud computing environment described with reference to FIGS. 10 and 11 to employ transfer learning in one or more machine learning models employed to generate molecular structures that exhibit one or more attributes of interest.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware based systems that perform the specified functions or acts or carry out combinations of special purpose hardware and computer instructions.

Figure 12:
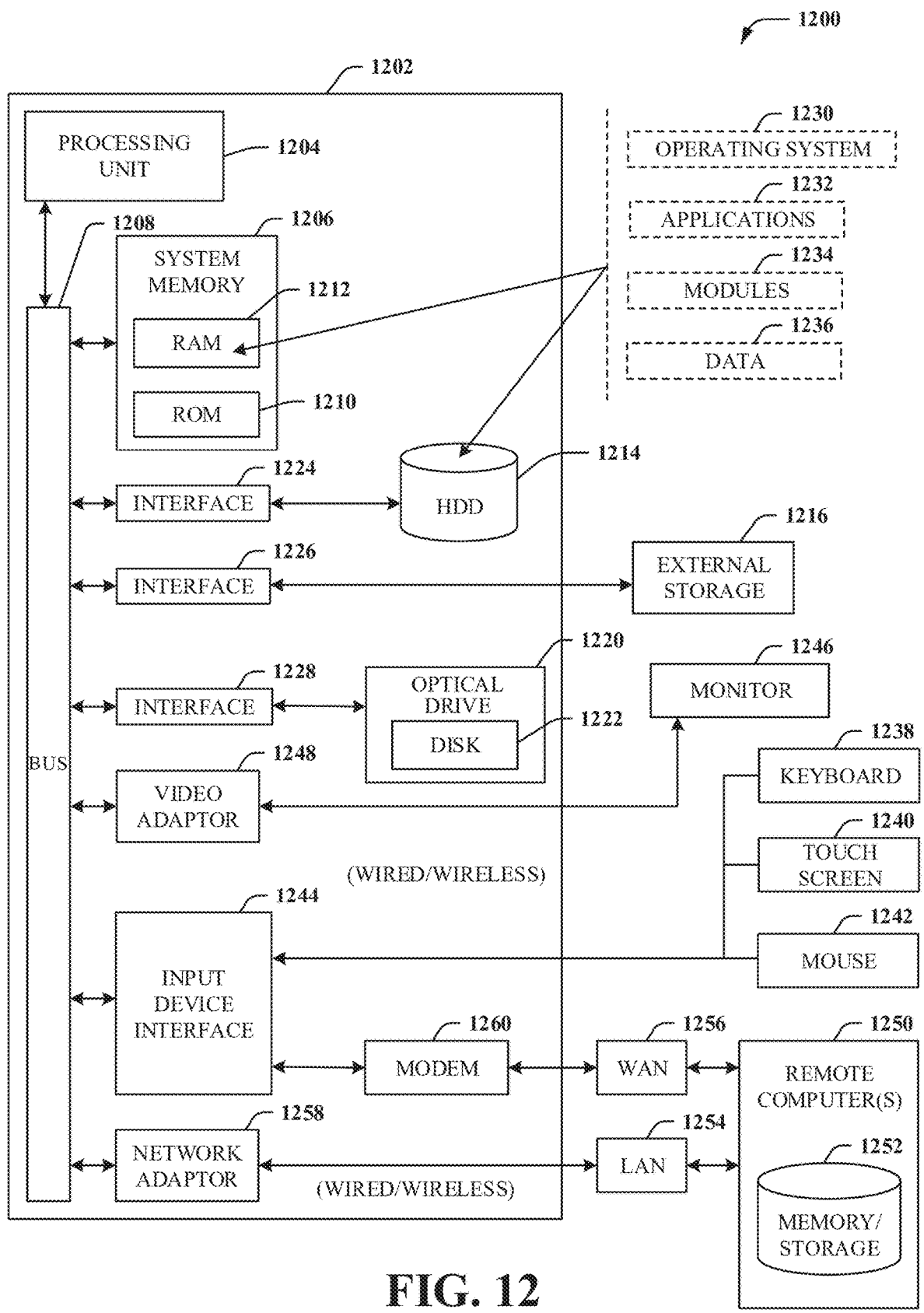
FIG. 12 illustrates a block diagram of an example, non-limiting operating environment in which one or more embodiments described herein can be facilitated.

In order to provide additional context for various embodiments described herein, FIG. 12 and the following discussion are intended to provide a general description of a suitable computing environment 1200 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things ("IoT") devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory ("RAM"), read only memory ("ROM"), electrically erasable programmable read only memory ("EEPROM"), flash memory or other memory technology, compact disk read only memory ("CD-ROM"), digital versatile disk ("DVD"), Blu-ray disc ("BD") or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 12, the example environment 1200 for implementing various embodiments of the aspects described herein includes a computer 1202, the computer 1202 including a processing unit 1204, a system memory 1206 and a system bus 1208. The system bus 1208 couples system components including, but not limited to, the system memory 1206 to the processing unit 1204. The processing unit 1204 can be any of various commercially available processors. Dual microprocessors and other multi-processor architectures can also be employed as the processing unit 1204.

The system bus 1208 can be any of several types of bus structure that can further interconnect to a memory bus (with or without a memory controller), a peripheral bus, and a local bus using any of a variety of commercially available bus architectures. The system memory 1206 includes ROM 1210 and RAM 1212. A basic input/output system ("BIOS") can be stored in a non-volatile memory such as ROM, erasable programmable read only memory ("EPROM"), EEPROM, which BIOS contains the basic routines that help to transfer information between elements within the computer 1202, such as during startup. The RAM 1212 can also include a high-speed RAM such as static RAM for caching data.

The computer 1202 further includes an internal hard disk drive ("HDD") 1214 (e.g., EIDE, SATA), one or more external storage devices 1216 (e.g., a magnetic floppy disk drive ("FDD") 1216, a memory stick or flash drive reader, a memory card reader, etc.) and an optical disk drive 1220 (e.g., which can read or write from a CD-ROM disc, a DVD, a BD, etc.). While the internal HDD 1214 is illustrated as located within the computer 1202, the internal HDD 1214 can also be configured for external use in a suitable chassis (not shown). Additionally, while not shown in environment 1200, a solid state drive ("SSD") could be used in addition to, or in place of, an HDD 1214. The HDD 1214, external storage device(s) 1216 and optical disk drive 1220 can be connected to the system bus 1208 by an HDD interface 1224, an external storage interface 1226 and an optical drive interface 1228, respectively. The interface 1224 for external drive implementations can include at least one or both of Universal Serial Bus ("USB") and Institute of Electrical and Electronics Engineers ("IEEE") 1394 interface technologies. Other external drive connection technologies are within contemplation of the embodiments described herein.

The drives and their associated computer-readable storage media provide nonvolatile storage of data, data structures, computer-executable instructions, and so forth. For the computer 1202, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1212, including an operating system 1230, one or more application programs 1232, other program modules 1234 and program data 1236. All or portions of the operating system, applications, modules, and/or data can also be cached in the RAM 1212. The systems and methods described herein can be implemented utilizing various commercially available operating systems or combinations of operating systems.

Computer 1202 can optionally comprise emulation technologies. For example, a hypervisor (not shown) or other intermediary can emulate a hardware environment for operating system 1230, and the emulated hardware can optionally be different from the hardware illustrated in FIG. 12. In such an embodiment, operating system 1230 can comprise one virtual machine ("VM") of multiple VMs hosted at computer 1202. Furthermore, operating system 1230 can provide runtime environments, such as the Java runtime environment or the .NET framework, for applications 1232. Runtime environments are consistent execution environments that allow applications 1232 to run on any operating system that includes the runtime environment. Similarly, operating system 1230 can support containers, and applications 1232 can be in the form of containers, which are lightweight, standalone, executable packages of software that include, e.g., code, runtime, system tools, system libraries and settings for an application.

Further, computer 1202 can be enable with a security module, such as a trusted processing module ("TPM"). For instance with a TPM, boot components hash next in time boot components, and wait for a match of results to secured values, before loading a next boot component. This process can take place at any layer in the code execution stack of computer 1202, e.g., applied at the application execution level or at the operating system ("OS") kernel level, thereby enabling security at any level of code execution.

A user can enter commands and information into the computer 1202 through one or more wired/wireless input devices, e.g., a keyboard 1238, a touch screen 1240, and a pointing device, such as a mouse 1242. Other input devices (not shown) can include a microphone, an infrared ("IR") remote control, a radio frequency ("RF") remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1204 through an input device interface 1244 that can be coupled to the system bus 1208, but can be connected by other interfaces, such as a parallel port, an IEEE 1394 serial port, a game port, a USB port, an IR interface, a BLUETOOTH® interface, etc.

A monitor 1246 or other type of display device can be also connected to the system bus 1208 via an interface, such as a video adapter 1248. In addition to the monitor 1246, a computer typically includes other peripheral output devices (not shown), such as speakers, printers, etc.

The computer 1202 can operate in a networked environment using logical connections via wired and/or wireless communications to one or more remote computers, such as a remote computer(s) 1250. The remote computer(s) 1250 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1252 is illustrated. The logical connections depicted include wired/wireless connectivity to a local area network ("LAN") 1254 and/or larger networks, e.g., a wide area network ("WAN") 1256. Such LAN and WAN networking environments are commonplace in offices and companies, and facilitate enterprise-wide computer networks, such as intranets, all of which can connect to a global communications network, e.g., the Internet.

When used in a LAN networking environment, the computer 1202 can be connected to the local network 1254 through a wired and/or wireless communication network interface or adapter 1258. The adapter 1258 can facilitate wired or wireless communication to the LAN 1254, which can also include a wireless access point ("AP") disposed thereon for communicating with the adapter 1258 in a wireless mode.

When used in a WAN networking environment, the computer 1202 can include a modem 1260 or can be connected to a communications server on the WAN 1256 via other means for establishing communications over the WAN 1256, such as by way of the Internet. The modem 1260, which can be internal or external and a wired or wireless device, can be connected to the system bus 1208 via the input device interface 1244. In a networked environment, program modules depicted relative to the computer 1202 or portions thereof, can be stored in the remote memory/storage device 1252. It will be appreciated that the network connections shown are example and other means of establishing a communications link between the computers can be used.

When used in either a LAN or WAN networking environment, the computer 1202 can access cloud storage systems or other network-based storage systems in addition to, or in place of, external storage devices 1216 as described above. Generally, a connection between the computer 1202 and a cloud storage system can be established over a LAN 1254 or WAN 1256 e.g., by the adapter 1258 or modem 1260, respectively. Upon connecting the computer 1202 to an associated cloud storage system, the external storage interface 1226 can, with the aid of the adapter 1258 and/or modem 1260, manage storage provided by the cloud storage system as it would other types of external storage. For instance, the external storage interface 1226 can be configured to provide access to cloud storage sources as if those sources were physically connected to the computer 1202.

The computer 1202 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity ("Wi-Fi") and BLUETOOTH® wireless technologies. Thus, the communication can be a predefined structure as with a conventional network or simply an ad hoc communication between at least two devices.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor, operably coupled to the memory, and that executes the computer executable components stored in the memory, wherein the computer executable components comprise:
a transfer learning component that trains a machine learning model to design molecules that satisfy defined criteria with respect to binding to proteins while having drug likeliness and synthetic accessibility, wherein the training comprises:
training, using unlabeled training data associated with target attributes of the molecules, an autoencoder of the machine learning model, to predict the target attributes of the molecules, and
jointly training, using first labeled training data for a first attribute of the target attributes having an amount of labeled training data exceeding a defined threshold, the autoencoder and at least one of a regressor or a first classifier of the machine learning model to predict the first attribute, wherein the joint training comprises learning, by the autoencoder, a latent space that is predictive of whether a molecular structure exhibits the first attribute.

2. The system of claim 1, wherein the autoencoder encodes the molecules into latent representations, and the training further comprises:
decoding, by a decoder of the of the machine learning model, the latent representations into reconstructed molecules,
determining one or more reconstruction loss values based on a comparison of the molecules and the reconstructed molecules, and
determining whether the autoencoder is trained based on the one or more reconstruction loss values.

3. The system of claim 1, wherein the autoencoder is an unconditional variational autoencoder.

4. The system of claim 2, wherein training further comprises:
training the decoder to decode the latent representations into the reconstructed molecules.

5. The system of claim 1, wherein the joint training further comprises training the autoencoder and at least one of the regressor or the first classifier using a training dataset that includes molecular structures of compounds that exhibit a second attribute.

6. The system of claim 5, wherein the target attributes further comprises the second attribute.

7. The system of claim 1, wherein the training further comprise:
training a second classifier of the machine learning model on the latent space learned by the autoencoder.

8. The system of claim 7, further comprising;
a model component that performs conditional generation of a molecule by executing the machine learning model with rejection sampling in the latent space using a density model and the second classifier.

9. A computer-implemented method, comprising:
training, by a system operatively coupled to a processor, a machine learning model to design molecules that satisfy defined criteria with respect to binding to proteins while having drug likeliness and synthetic accessibility, wherein the training comprises:
training, using unlabeled training data associated with target attributes of the molecules, an autoencoder of the machine learning model, to predict the target attributes of the molecules, and
jointly training, using first labeled training data for a first attribute of the target attributes having an amount of labeled training data exceeding a defined threshold, the autoencoder and at least one of a regressor or a first classifier of the machine learning model to predict the first attribute, wherein the joint training comprises learning, by the autoencoder, a latent space that is predictive of whether a molecular structure exhibits the first attribute.

10. The computer-implemented method of claim 9, wherein the autoencoder encodes the molecules into latent representations, and the training further comprises:
decoding, by a decoder of the of the machine learning model, the latent representations into reconstructed molecules,
determining one or more reconstruction loss values based on a comparison of the molecules and the reconstructed molecules, and
determining whether the autoencoder is trained based on the one or more reconstruction loss values.

11. The computer-implemented method of claim 9, wherein the autoencoder is an unconditional variational autoencoder.

12. The computer-implemented method of claim 10, wherein training further comprises:
training the decoder to decode the latent representations into the reconstructed molecules.

13. The computer-implemented method of claim 9, wherein the joint training further comprises:
training the autoencoder and at least one of the regressor or the first classifier using a training dataset that includes molecular structures of compounds that exhibit a second attribute.

14. The computer-implemented method of claim 13, wherein the target attributes further comprise and the second attribute.

15. The computer-implemented method of claim 9, wherein the training further comprises training a second classifier of the machine learning model on the latent space learned by the autoencoder; and
the computer-implemented method further comprises performing, by the system, a conditional generation of a molecule by executing the machine learning model with rejection sampling in the latent space using a density model and the second classifier.

16. A computer program product for autonomous discovery of a compound, the computer program product comprising a computer readable storage medium having program instructions embodied therewith, the program instructions executable by a processor to cause the processor to:
train, by the processor, a machine learning model to design molecules that satisfy defined criteria with respect to binding to proteins while having drug likeliness and synthetic accessibility, wherein the training comprises:
training, using unlabeled training data associated with target attributes of the molecules, an autoencoder of the machine learning model, to predict the target attributes of the molecules, and
jointly training, using first labeled training data for a first attribute of the target attributes having an amount of labeled training data exceeding a defined threshold, the autoencoder and at least one of a regressor or a first classifier of the machine learning model to predict the first attribute, wherein the joint training comprises learning, by the autoencoder, a latent space that is predictive of whether a molecular structure exhibits the first attribute.

17. The computer program product of claim 16, wherein the autoencoder encodes the molecules into latent representations, and the training further comprises:
decoding, by a decoder of the of the machine learning model, the latent representations into reconstructed molecules,
determining one or more reconstruction loss values based on a comparison of the molecules and the reconstructed molecules, and
determining whether the autoencoder is trained based on the one or more reconstruction loss values.

18. The computer program product of claim 17, wherein the training further comprises:
training the decoder to decode the latent representations into the reconstructed molecules.

19. The computer program product of claim 16, wherein the joint training further comprises:
training the autoencoder and at least one of the regressor or the first classifier using a training dataset that includes molecular structures of compounds that exhibit a second attribute, wherein the target attributes further comprise the second attribute.

20. The computer program product of claim 16, wherein the training further comprises training a second classifier of the machine learning model on the latent space learned by the autoencoder; and
wherein the program instructions further cause the processor to:
perform, by the processor, a conditional generation of a molecule by executing the machine learning model with rejection sampling in the latent space using a density model and the second classifier.

\* \* \* \* \*